(12) United States Patent
Ma et al.

(10) Patent No.: US 9,808,256 B2
(45) Date of Patent: Nov. 7, 2017

(54) ELECTROLYTIC DETACHMENT ELEMENTS FOR IMPLANT DELIVERY SYSTEMS

(71) Applicant: COVIDIEN LP, Mansfield, MA (US)

(72) Inventors: Jianlu Ma, Irvine, CA (US); Vincent Divino, Mission Viejo, CA (US)

(73) Assignee: Covidien LP, Mansfield, MA (US)

( * ) Notice: Subject to any disclaimer, the term of this patent is extended or adjusted under 35 U.S.C. 154(b) by 581 days.

(21) Appl. No.: 14/454,880

(22) Filed: Aug. 8, 2014

(65) Prior Publication Data

US 2016/0038152 A1    Feb. 11, 2016

(51) Int. Cl.
| | |
|---|---|
| *A61B 17/12* | (2006.01) |
| *A61B 17/00* | (2006.01) |
| *A61B 90/00* | (2016.01) |

(52) U.S. Cl.
CPC .. *A61B 17/12172* (2013.01); *A61B 17/12113* (2013.01); *A61B 2017/00526* (2013.01);
(Continued)

(58) Field of Classification Search
CPC ........ A61B 17/12113; A61B 17/12109; A61B 17/12172; A61B 2017/12063
See application file for complete search history.

(56) References Cited

U.S. PATENT DOCUMENTS

| | | |
|---|---|---|
| 5,108,407 A | 4/1992 | Geremia et al. |
| 5,122,136 A | 6/1992 | Guglielmi et al. |

(Continued)

FOREIGN PATENT DOCUMENTS

| | | |
|---|---|---|
| DE | 4445715 A1 | 6/1996 |
| DE | 10118017 | 10/2002 |

(Continued)

OTHER PUBLICATIONS

U.S. Appl. No. 14/454,930, filed Aug. 8, 2014.
European Search Report and Opinion dated Mar. 9, 2016; European Application No. 15180213.9; 14 pages.

*Primary Examiner* — Tuan V Nguyen
*Assistant Examiner* — Chima Igboko
(74) *Attorney, Agent, or Firm* — Mark Kertz

(57) ABSTRACT

Detachment of a medical device from a delivery assembly can focus activity of electrolytic detachment to enhance detachment procedures. Electrolytic activity can be focused by insulating nearby areas of a core wire and pre-treating a detachment zone to reduce crystallinity of the detachment zone. Such a delivery system, can include an electrolytically corrodible core wire comprising a proximal portion, a distal portion, and a detachment zone between the proximal portion and the distal portion; a proximal insulating layer annularly contacting the proximal portion; a coil helically winding about and contacting at least a portion of the proximal insulating layer; a tube annularly contacting at least a portion of the helical coil; a distal insulating layer annularly contacting the distal portion; and a hub of an implant annularly contacting at least a portion of the distal insulating layer; wherein a distal end of the proximal insulating layer and a proximal end of the distal insulating layer are axially spaced apart to expose the detachment zone.

15 Claims, 6 Drawing Sheets

(52) U.S. Cl.
CPC .............. *A61B 2017/12063* (2013.01); *A61B 2090/3966* (2016.02)

(56) References Cited

U.S. PATENT DOCUMENTS

| | | | |
|---|---|---|---|
| 5,250,071 A | 10/1993 | Palermo | |
| 5,354,295 A | 10/1994 | Guglielmi et al. | |
| 5,370,653 A | 12/1994 | Cragg | |
| 5,423,829 A | 6/1995 | Pham et al. | |
| 5,522,836 A | 6/1996 | Palermo | |
| 5,540,680 A | 7/1996 | Guglielmi et al. | |
| 5,624,449 A | 4/1997 | Pham et al. | |
| 5,658,308 A | 8/1997 | Snyder | |
| 5,690,667 A | 11/1997 | Gia | |
| 5,733,329 A | 3/1998 | Wallace et al. | |
| 5,743,905 A | 4/1998 | Eder et al. | |
| 5,749,894 A | 5/1998 | Engelson | |
| 5,766,629 A | 6/1998 | Cho et al. | |
| 5,800,455 A | 9/1998 | Palermo et al. | |
| 5,851,206 A | 12/1998 | Guglielmi et al. | |
| 5,853,418 A | 12/1998 | Ken et al. | |
| 5,855,578 A | 1/1999 | Guglielmi et al. | |
| 5,891,128 A * | 4/1999 | Gia .................. | A61B 17/12022 606/1 |
| 5,895,385 A | 4/1999 | Guglielmi et al. | |
| 5,916,235 A | 6/1999 | Guglielmi | |
| 5,919,187 A | 7/1999 | Guglielmi et al. | |
| 5,925,037 A | 7/1999 | Guglielmi et al. | |
| 5,925,059 A | 7/1999 | Palermo et al. | |
| 5,928,226 A | 7/1999 | Guglielmi et al. | |
| 5,935,145 A | 8/1999 | Villar et al. | |
| 5,941,888 A | 8/1999 | Wallace et al. | |
| 5,944,714 A | 8/1999 | Guglielmi et al. | |
| 5,947,962 A | 9/1999 | Guglielmi et al. | |
| 5,947,963 A | 9/1999 | Guglielmi | |
| 5,964,797 A | 10/1999 | Ho | |
| 5,976,126 A | 11/1999 | Guglielmi | |
| 5,984,929 A | 11/1999 | Bashiri et al. | |
| 6,010,498 A | 1/2000 | Guglielmi | |
| 6,013,084 A | 1/2000 | Ken et al. | |
| 6,059,779 A | 5/2000 | Mills | |
| 6,063,070 A | 5/2000 | Eder | |
| 6,063,104 A | 5/2000 | Villar et al. | |
| 6,066,133 A | 5/2000 | Guglielmi et al. | |
| 6,077,260 A | 6/2000 | Wheelock et al. | |
| 6,083,220 A | 7/2000 | Guglielmi et al. | |
| 6,123,714 A | 9/2000 | Gia et al. | |
| 6,136,015 A | 10/2000 | Kurz et al. | |
| 6,146,373 A | 11/2000 | Cragg et al. | |
| 6,156,061 A | 12/2000 | Wallace et al. | |
| 6,165,178 A | 12/2000 | Bashiri et al. | |
| 6,168,592 B1 | 1/2001 | Kupiecki et al. | |
| 6,168,615 B1 | 1/2001 | Ken et al. | |
| 6,168,618 B1 | 1/2001 | Frantzen | |
| 6,193,728 B1 | 2/2001 | Ken et al. | |
| 6,238,403 B1 | 5/2001 | Greene, Jr. et al. | |
| 6,241,691 B1 | 6/2001 | Ferrera et al. | |
| 6,280,457 B1 | 8/2001 | Wallace et al. | |
| 6,296,622 B1 | 10/2001 | Kurz et al. | |
| 6,299,619 B1 | 10/2001 | Greene, Jr. et al. | |
| 6,306,153 B1 | 10/2001 | Kurz et al. | |
| 6,371,972 B1 | 4/2002 | Wallace et al. | |
| 6,409,721 B1 | 6/2002 | Wheelock et al. | |
| 6,416,373 B1 | 7/2002 | Kolb et al. | |
| 6,425,893 B1 | 7/2002 | Guglielmi | |
| 6,425,914 B1 | 7/2002 | Wallace et al. | |
| 6,468,266 B1 | 10/2002 | Bashiri et al. | |
| 6,468,301 B1 | 10/2002 | Amplatz et al. | |
| 6,478,773 B1 | 11/2002 | Gandhi et al. | |
| 6,485,524 B2 | 11/2002 | Strecker | |
| 6,486,266 B2 | 11/2002 | Amano et al. | |
| 6,511,468 B1 | 1/2003 | Cragg et al. | |
| 6,533,801 B2 | 3/2003 | Wallace et al. | |
| 6,558,367 B1 | 5/2003 | Cragg et al. | |
| 6,589,230 B2 | 7/2003 | Gia et al. | |
| 6,589,236 B2 | 7/2003 | Wheelock et al. | |
| 6,602,261 B2 | 8/2003 | Greene, Jr. et al. | |
| 6,620,152 B2 | 9/2003 | Guglielmi | |
| 6,623,493 B2 | 9/2003 | Wallace et al. | |
| 6,723,112 B2 | 4/2004 | Ho et al. | |
| 6,743,251 B1 | 6/2004 | Eder | |
| 6,835,185 B2 | 12/2004 | Ramzipoor et al. | |
| 6,905,503 B2 | 6/2005 | Gifford, III et al. | |
| 6,936,055 B1 | 8/2005 | Ken et al. | |
| 6,953,473 B2 | 10/2005 | Porter | |
| 6,964,657 B2 | 11/2005 | Cragg et al. | |
| 6,966,892 B2 | 11/2005 | Gandhi et al. | |
| 7,014,645 B2 | 3/2006 | Greene, Jr. et al. | |
| 7,083,567 B2 | 8/2006 | Mawad | |
| 7,128,736 B1 | 10/2006 | Abrams et al. | |
| 7,166,122 B2 | 1/2007 | Aganon et al. | |
| 7,169,172 B2 | 1/2007 | Levine et al. | |
| 7,198,613 B2 | 4/2007 | Gandhi et al. | |
| 7,238,194 B2 | 7/2007 | Monstadt et al. | |
| 7,255,707 B2 | 8/2007 | Ramzipoor et al. | |
| 7,300,458 B2 | 11/2007 | Henkes et al. | |
| 7,323,000 B2 | 1/2008 | Monstdt et al. | |
| 7,331,974 B2 | 2/2008 | Schaefer et al. | |
| 7,485,122 B2 | 2/2009 | Teoh | |
| 7,524,322 B2 | 4/2009 | Monstdt et al. | |
| 7,608,089 B2 | 10/2009 | Wallace et al. | |
| RE41,029 E | 12/2009 | Guglielmi et al. | |
| 7,651,513 B2 | 1/2010 | Teoh et al. | |
| 7,695,484 B2 | 4/2010 | Wallace et al. | |
| 7,879,064 B2 | 2/2011 | Monstadt et al. | |
| 7,896,899 B2 | 3/2011 | Patterson et al. | |
| 7,938,845 B2 | 5/2011 | Aganon et al. | |
| 8,002,789 B2 | 8/2011 | Ramzipoor et al. | |
| RE42,756 E | 9/2011 | Guglielmi et al. | |
| 8,016,869 B2 | 9/2011 | Nikolchev | |
| 8,021,416 B2 | 9/2011 | Abrams | |
| 8,048,104 B2 | 11/2011 | Monstadt et al. | |
| RE43,311 E | 4/2012 | Wallace et al. | |
| 8,157,855 B2 | 4/2012 | Eidenschink et al. | |
| 8,202,292 B2 | 6/2012 | Kellett | |
| 8,221,396 B2 | 7/2012 | Dehnad et al. | |
| 8,221,483 B2 | 7/2012 | Ford et al. | |
| 8,273,116 B2 | 9/2012 | Licata et al. | |
| 8,298,256 B2 | 10/2012 | Gandhi et al. | |
| 8,328,860 B2 | 12/2012 | Strauss et al. | |
| 8,372,110 B2 | 2/2013 | Monstadt et al. | |
| 8,398,671 B2 | 3/2013 | Chen et al. | |
| 8,480,701 B2 | 7/2013 | Monstadt | |
| 8,562,667 B2 | 10/2013 | Cox | |
| 8,597,321 B2 | 12/2013 | Monstadt et al. | |
| 8,632,584 B2 | 1/2014 | Henkes et al. | |
| 8,641,746 B2 | 2/2014 | Andreas et al. | |
| 8,641,777 B2 | 2/2014 | Strauss et al. | |
| 8,652,163 B2 | 2/2014 | Padilla et al. | |
| 8,657,870 B2 | 2/2014 | Turovskiy et al. | |
| 8,715,312 B2 | 5/2014 | Burke et al. | |
| 8,721,625 B2 | 5/2014 | Klint | |
| 8,728,142 B2 | 5/2014 | Gandhi et al. | |
| 8,777,978 B2 | 7/2014 | Strauss et al. | |
| 8,777,979 B2 | 7/2014 | Shrivastava et al. | |
| 8,795,320 B2 | 8/2014 | Strauss et al. | |
| 8,795,321 B2 | 8/2014 | Strauss et al. | |
| 8,801,747 B2 | 8/2014 | Strauss et al. | |
| 8,845,676 B2 | 9/2014 | Monstadt et al. | |
| 8,864,790 B2 | 10/2014 | Strauss et al. | |
| 8,870,909 B2 | 10/2014 | Cox | |
| 8,876,863 B2 | 11/2014 | Eskridge | |
| 8,900,285 B2 | 12/2014 | Licata | |
| 8,915,950 B2 | 12/2014 | Cam et al. | |
| 8,926,681 B2 | 1/2015 | Levy et al. | |
| 8,932,317 B2 | 1/2015 | Marks et al. | |
| 8,940,011 B2 | 1/2015 | Teoh et al. | |
| 8,974,509 B2 | 3/2015 | Licata | |
| 8,974,513 B2 | 3/2015 | Ford et al. | |
| 8,992,563 B2 | 3/2015 | Chen | |
| 8,998,926 B2 | 4/2015 | Pomeranz | |
| 9,039,749 B2 | 5/2015 | Shrivastava et al. | |
| 9,050,095 B2 | 6/2015 | Monstadt et al. | |
| 9,055,948 B2 | 6/2015 | Jaeger et al. | |

(56) References Cited

U.S. PATENT DOCUMENTS

| | | |
|---|---|---|
| 2002/0151883 A1 | 10/2002 | Guglielmi |
| 2003/0014073 A1 | 1/2003 | Bashiri et al. |
| 2003/0040733 A1 | 2/2003 | Cragg et al. |
| 2003/0176857 A1 | 9/2003 | Lee |
| 2003/0225365 A1 | 12/2003 | Greff et al. |
| 2004/0002731 A1 | 1/2004 | Aganon et al. |
| 2004/0225279 A1 | 11/2004 | Raymond |
| 2004/0236344 A1 | 11/2004 | Monstadt et al. |
| 2005/0079196 A1 | 4/2005 | Henkes et al. |
| 2006/0036281 A1 | 2/2006 | Patterson et al. |
| 2006/0135986 A1 | 6/2006 | Wallace et al. |
| 2006/0271097 A1 | 11/2006 | Ramzipoor et al. |
| 2007/0073334 A1 | 3/2007 | Ramzipoor |
| 2008/0045922 A1 | 2/2008 | Cragg et al. |
| 2008/0051803 A1 | 2/2008 | Monjtadt et al. |
| 2008/0103585 A1 | 5/2008 | Monstadt et al. |
| 2008/0125855 A1 | 5/2008 | Henkes et al. |
| 2008/0221666 A1 | 9/2008 | Licata et al. |
| 2008/0228215 A1 | 9/2008 | Strauss et al. |
| 2008/0228216 A1 | 9/2008 | Strauss et al. |
| 2008/0319532 A1 | 12/2008 | Monstadt et al. |
| 2009/0143786 A1 | 6/2009 | Bashiri et al. |
| 2009/0254111 A1 | 10/2009 | Monstadt et al. |
| 2010/0023105 A1 | 1/2010 | Levy et al. |
| 2010/0030200 A1 | 2/2010 | Strauss et al. |
| 2010/0049165 A1 | 2/2010 | Sutherland et al. |
| 2010/0063572 A1 | 3/2010 | Teoh et al. |
| 2010/0076479 A1 | 3/2010 | Monstadt |
| 2010/0256666 A1 | 10/2010 | Chen et al. |
| 2010/0331948 A1 | 12/2010 | Turovskiy et al. |
| 2011/0098814 A1 | 4/2011 | Monstadt et al. |
| 2011/0106128 A1 | 5/2011 | Chen |
| 2011/0118768 A1 | 5/2011 | Tran et al. |
| 2011/0118777 A1 | 5/2011 | Patterson et al. |
| 2011/0184453 A1 | 7/2011 | Levy et al. |
| 2012/0010648 A1 | 1/2012 | Monstadt et al. |
| 2012/0209310 A1* | 8/2012 | Chen ............... A61B 17/12022 606/195 |
| 2012/0271344 A1 | 10/2012 | Ford et al. |
| 2013/0138198 A1 | 5/2013 | Aporta et al. |
| 2013/0184743 A1 | 7/2013 | Chen et al. |
| 2013/0211492 A1 | 8/2013 | Schneider et al. |
| 2014/0005651 A1 | 1/2014 | Eskridge |
| 2014/0039535 A1 | 2/2014 | Eskuri |
| 2014/0135818 A1 | 5/2014 | Gandhi et al. |
| 2014/0142608 A1 | 5/2014 | Eskridge et al. |
| 2014/0148843 A1 | 5/2014 | Strauss et al. |
| 2014/0163604 A1 | 6/2014 | Monstadt et al. |
| 2014/0236217 A1 | 8/2014 | Gandhi et al. |
| 2014/0277092 A1 | 9/2014 | Teoh et al. |
| 2014/0277094 A1 | 9/2014 | Chen et al. |
| 2014/0288633 A1 | 9/2014 | Burke et al. |
| 2014/0371839 A1 | 12/2014 | Henkes et al. |
| 2015/0005804 A1 | 1/2015 | Franano et al. |
| 2015/0057700 A1 | 2/2015 | Chen et al. |
| 2015/0066073 A1 | 3/2015 | Ma |
| 2015/0105817 A1 | 4/2015 | Marchand et al. |
| 2015/0133990 A1 | 5/2015 | Davidson |
| 2015/0142042 A1 | 5/2015 | Cox |
| 2015/0150563 A1 | 6/2015 | Marchand et al. |
| 2015/0157331 A1 | 6/2015 | Levy et al. |
| 2015/0164665 A1 | 6/2015 | Cam et al. |
| 2015/0173771 A1 | 6/2015 | Marks et al. |

FOREIGN PATENT DOCUMENTS

| | | |
|---|---|---|
| EP | 484468 A1 | 5/1992 |
| EP | 719522 A1 | 7/1996 |
| EP | 726745 A1 | 8/1996 |
| EP | 0739606 A1 | 10/1996 |
| EP | 803230 A2 | 10/1997 |
| EP | 807410 A2 | 11/1997 |
| EP | 861634 A2 | 9/1998 |
| EP | 1005837 A2 | 6/2000 |
| EP | 1009295 A1 | 6/2000 |
| EP | 1227760 A1 | 8/2002 |
| EP | 1329196 A1 | 7/2003 |
| EP | 1420701 A1 | 5/2004 |
| EP | 1843710 A1 | 10/2007 |
| EP | 1884208 A1 | 2/2008 |
| EP | 1951129 A2 | 8/2008 |
| EP | 2124763 A2 | 12/2009 |
| EP | 2146651 A2 | 1/2010 |
| EP | 2227163 A1 | 9/2010 |
| EP | 2334242 A1 | 6/2011 |
| EP | 2415424 A2 | 2/2012 |
| EP | 2575697 A1 | 4/2013 |
| EP | 2668914 A1 | 12/2013 |
| EP | 2781196 A2 | 9/2014 |
| EP | 2859854 A1 | 4/2015 |
| JP | 2005500121 A | 1/2005 |
| WO | WO-91/13592 A1 | 9/1991 |
| WO | WO-99/09894 A1 | 3/1999 |
| WO | WO-2012/166804 A1 | 12/2012 |
| WO | WO-2013/119332 A2 | 8/2013 |

* cited by examiner

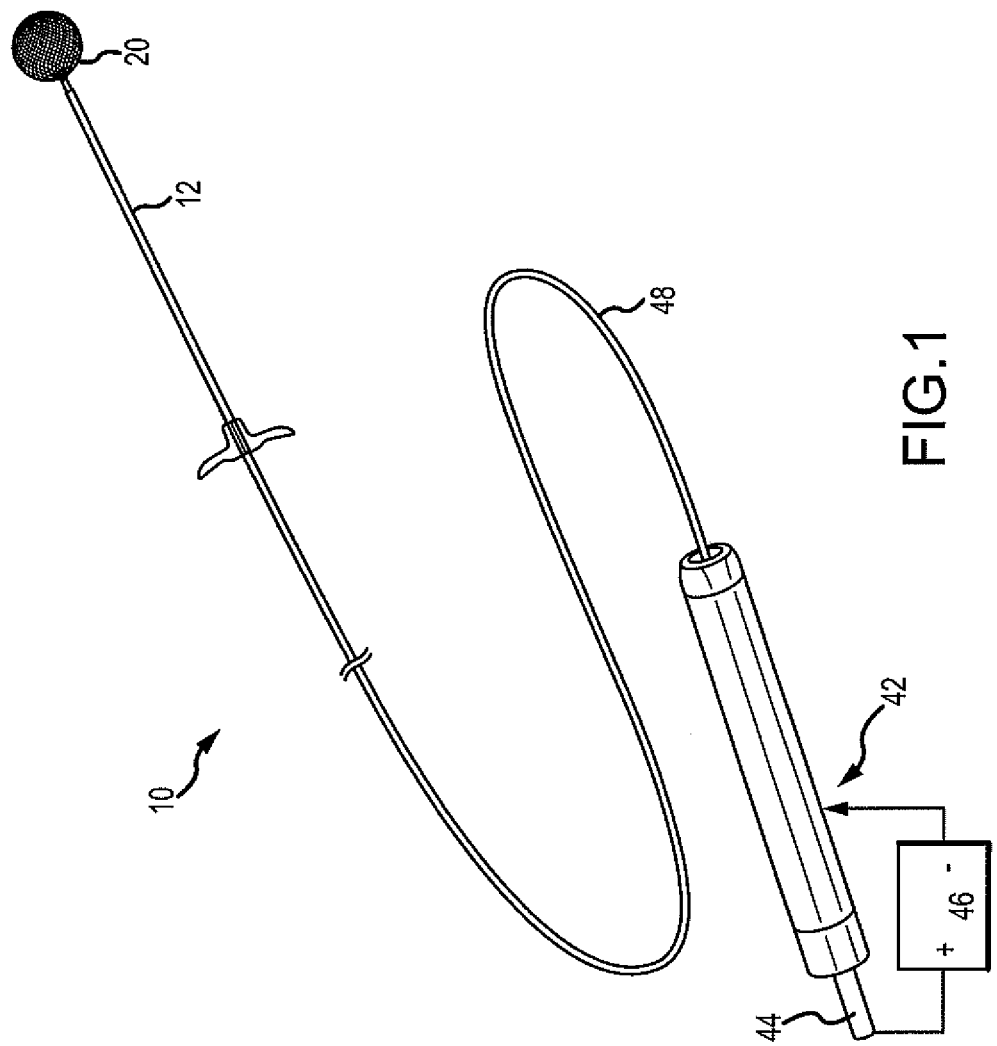

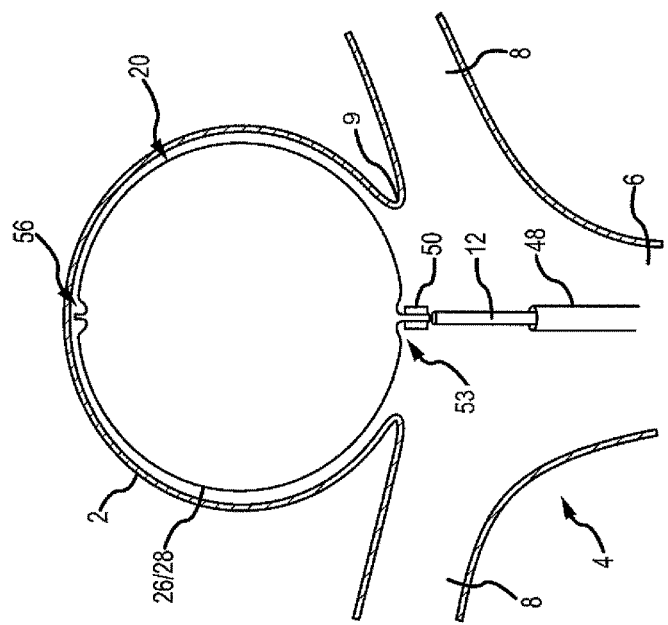
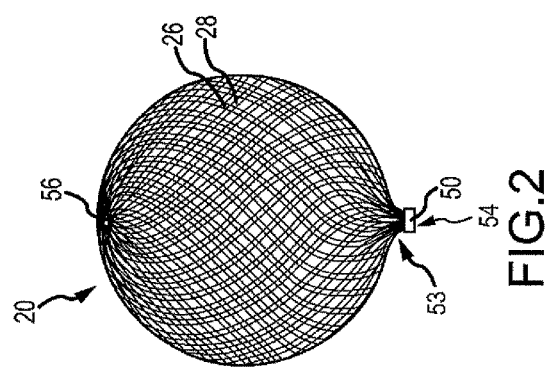

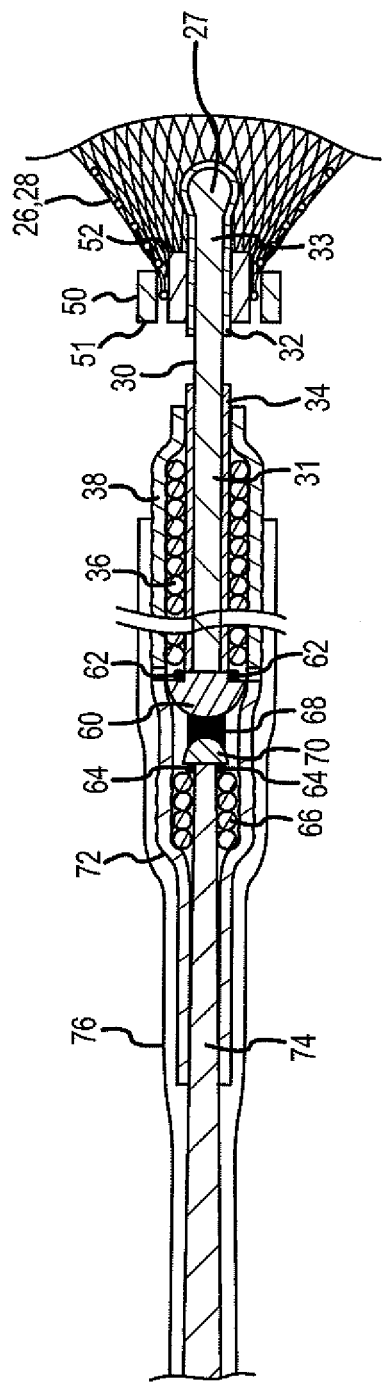

ELECTROLYTIC DETACHMENT ELEMENTS FOR IMPLANT DELIVERY SYSTEMS

FIELD

The subject technology relates to delivery of implantable devices.

BACKGROUND

The use of endovascular techniques for the implantation of medical devices and the occlusion of body cavities such as arteries, veins, fallopian tubes or vascular deformities is known in the art. For example, occlusion of vascular aneurysms can be performed using an implantable device, such as an intrasaccular implant, which is introduced with the aid of an endovascular delivery wire through a catheter. Once moved to the treatment site, the intrasaccular implant can be moved into the aneurysm cavity to occlude the aneurysm.

The severance of the intrasaccular implant from the endovascular delivery wire can be particularly problematic. On the one hand, the device must be as small as possible to be guided through the fine bore of the catheter to its destination, while on the other hand it must bring about a reliable severance of the intrasaccular implant. Absent a reliable severance of the intrasaccular implant, withdrawal of the delivery wire and catheter may cause unintended removal of the intrasaccular implant from the cavity to be occluded and thus injure and/or rupture of the wall of the cavity or vessel.

Traditional mechanical methods for the severance of intrasaccular implants from the insertion means do not take much time to perform. However, the necessary rigidity of the technical features of the connection between the intrasaccular implant and the introduction means can impede the introduction of the implant. Furthermore, the low load carrying capacity of the connection due to its rigidity entails an appreciable risk of premature detachment of the insertion means from the occluding implant. Moreover, in the case of mechanical separation of the inserting wire and the intrasaccular implant, energy must be transmitted (e.g., by rotation of the inserting wire), which may cause the implant to be dislodged out of the correct position.

Traditional electrolytic severance of the intrasaccular implant involves using an electrolytically corrodible design on the end of the delivery wire at the connection between the delivery wire and the intrasaccular implant. Such a device can elegantly make use of the voltage applied to the intrasaccular implant serving as an anode for electro-thrombization. However, the connection of the implant to the delivery wire is limited by the requirements of the electrolytically corrodible region. For example, the only materials that can be utilized are those which have a sufficiently high degree of strength to enable reliable guidance of the occluding wire through the delivery wire. The selection of materials for forming the point of eventual electrolytic severance is consequently extremely limited.

In the case of traditional devices for the electrolytic severance of intrasaccular implants, the intrasaccular implant and the delivery wire are not produced integrally, but instead are produced mechanically connected with each other. This design has the inherent disadvantage that the delivery wire must be tapered toward its end in an involved grinding operation in order to ensure sufficient strength in the proximal zone of the delivery wire and to facilitate electrolytic, corrosive severance of the wire end in the distal part of the delivery wire. In order to ensure sufficient strength of the connection point, the corrodible zone of the end of the delivery wire must not have a diameter below a certain minimum value since it is subjected to a high flexural load. The corrodible wire end representing the connection point between the intrasaccular implant and the delivery wire can be consequently extremely rigid and require a relatively long time for electrolytic corrosive severance.

SUMMARY

Electrolytic severance of the implantable medical devices can involve using an electrolytically corrodible design on the end of a delivery wire at the connection between the delivery wire and the medical device. Such a device can elegantly make use of the voltage applied to the intrasaccular implant serving as an anode for electro-thrombization.

According to some embodiments, a delivery system includes an electrolytically corrodible core wire comprising a proximal portion, a distal portion, and a detachment zone between the proximal portion and the distal portion; a proximal insulating layer annularly contacting the proximal portion; a coil helically winding about and contacting at least a portion of the proximal insulating layer; a tube annularly contacting at least a portion of the helical coil; a distal insulating layer annularly contacting the distal portion; and a hub of an implant annularly contacting at least a portion of the distal insulating layer; wherein a distal end of the proximal insulating layer and a proximal end of the distal insulating layer can be axially spaced apart to expose the detachment zone.

The detachment zone can have an axial length that is less than 0.010 inches. The detachment zone can have an axial length greater than or equal to 0.005 inches and less than 0.010 inches. The core wire can include a distalmost end that is axially coterminous with (i) a distalmost end of the distal insulating layer and (ii) a distalmost end of the hub. The detachment zone can be axially between the proximal portion and the distal portion. The proximal portion and the distal portion each can have a microstructure with a crystallinity that is greater than a crystallinity of a microstructure of the detachment zone. The detachment zone can include a microstructure that is more amorphous than each of (i) a microstructure of the proximal portion and (ii) a microstructure of the distal portion. The core wire can provide an anchor end that is distal to a distalmost end of the hub, the anchor end having a maximum cross-sectional dimension that is greater than an inner cross-sectional dimension of a lumen of the hub.

According to some embodiments, a delivery system includes an electrolytically corrodible core wire comprising a proximal portion, a distal portion, and a detachment zone between the proximal portion and the distal portion; a proximal insulating layer annularly contacting a proximal portion; and a distal insulating layer annularly contacting a distal portion; wherein a distal end of the proximal insulating layer and a proximal end of the distal insulating layer can be axially spaced apart to expose the detachment zone; wherein the detachment zone comprises a microstructure that is more amorphous than each of (i) a microstructure of the proximal portion and (ii) a microstructure of the distal portion.

The proximal portion, the detachment zone, and the distal portion can be of a conductive material. The detachment zone can be axially between the proximal portion and the distal portion. The proximal portion and the distal portion each can have a microstructure with a crystallinity that is greater than a crystallinity of a microstructure of the detachment zone. The delivery system can further include a coil helically winding about and contacting at least a portion of the proximal insulating layer; and a tube annularly contacting at least a portion of the helical coil. The delivery system can further include a hub of an implant annularly contacting at least a portion of the distal insulating layer. The detachment zone can have an axial length that is less than 0.010 inches. The detachment zone can have an axial length greater than or equal to 0.005 inches and less than 0.010 inches. The core wire can provide an anchor end that is distal to a distalmost end of the hub, the anchor end having a maximum cross-sectional dimension that is greater than an inner cross-sectional dimension of a lumen of the hub.

A method of forming an assembly can include: providing an electrolytically corrodible core wire comprising a proximal portion, a distal portion, and a detachment zone between the proximal portion and the distal portion, the distal portion being attached to an implant; annularly covering the proximal portion with a proximal insulating layer; annularly covering the distal portion with a distal insulating layer; treating the detachment zone to produce a microstructure in the detachment zone that is more amorphous than each of (i) a microstructure of the proximal portion and (ii) a microstructure of the distal portion.

The proximal portion, the detachment zone, and the distal portion can be of a conductive material. The detachment zone can be axially between the proximal portion and the distal portion. The treating can include applying laser energy to the detachment zone.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

FIG. 1 shows a perspective view providing an overview of a treatment system, in accordance with one or more embodiments of the present disclosure.

FIG. 2 shows a perspective side view of a braid ball, in accordance with one or more embodiments of the present disclosure.

FIG. 3 shows a side-sectional view of a braid ball implant deployed within a bifurcation aneurysm, in accordance with one or more embodiments of the present disclosure.

FIG. 7 shows a sectional view of a distal end of a delivery system, in accordance with one or more embodiments of the present disclosure.

DETAILED DESCRIPTION

Figure 4:
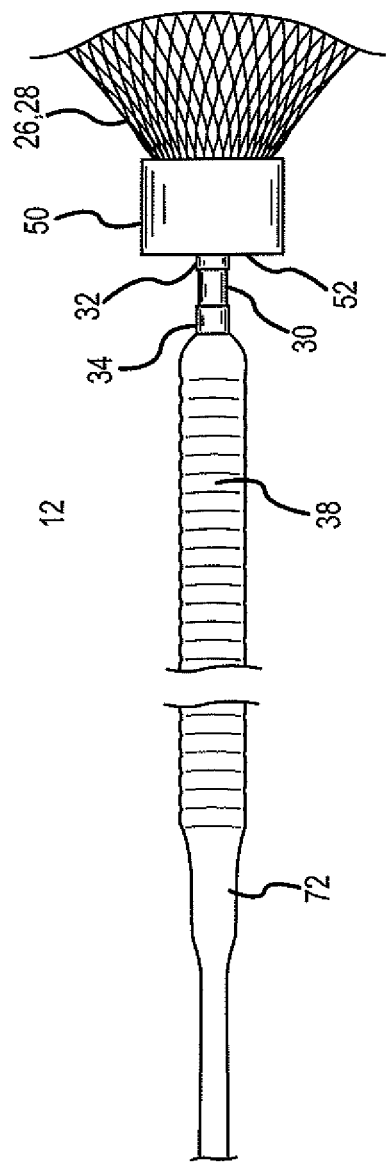
FIG. 4 shows a side view of a distal end of a delivery system, in accordance with one or more embodiments of the present disclosure.

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

In accordance with some embodiments disclosed herein is the realization that detachment of a medical device from a delivery assembly can be improved by enhancing features to focus the electrolytic corrosion activity. Thus, various embodiments provide for detachment zones that can facilitate electrolytic detachment of a delivery mechanism, making the detachment process faster and more reliable.

The medical device can be implanted in body cavities or blood vessels. In addition to the medical device, the delivery system can comprise a voltage source, a cathode, and a catheter. The medical device can be slid in the catheter in the longitudinal direction. A delivery wire may engage the medical device and be adapted to serve as an anode, such that a portion of the delivery wire is designed to be electrolytically corroded at one or more points so that while in contact with a body fluid, one or more portions of the medical device may be released from the delivery wire.

According to some embodiments, FIG. 1 presents an overview of a treatment system 10 including an implant 20 and a handle 42. The handle 42 shown provides proximal access to a delivery wire that engages the implant 20 at a distal end. The catheter/pusher shaft 12 can include a simple extrusion (e.g., PTFE, FEP, PEEK, etc.) or can be constructed using conventional catheter construction techniques and include a liner, braid support and outer jacket (not shown). A loading sheath 48 is typically provided over the shaft of a pusher 12.

A power supply 46 may be coupled to a proximal portion of the delivery wire 44. The power supply 46 may also be coupled to a proximal portion of the handle 42 or to the patient. A current can flow from the power supply 46, to a detachment zone at or near the implant 20, and to a return path via the catheter shaft 12 (and/or another structure extending near the detachment zone. Alternatively, the current from the detachment zone may flow to the patient, and subsequently to ground or to the power supply 46. Power supply 46, for example, may be a direct current power supply, an alternating current power supply, or a power supply switchable between a direct current and an alternating current. A positive terminal of a direct current power supply, as shown in FIG. 1, may be coupled to the proximal portion of the delivery wire 44 and a negative terminal of a direct current power supply may be coupled to the proximal portion of the handle 42. Power supply 46 may provide a current through the treatment system 10 to initiate an electrolytic process during use of the assembly in a fluid medium such as a bloodstream, which may be used as an electrolyte. A power supply, such as an alternating or direct current power supply, may additionally be used to initiate an electrothrombosis process.

According to some embodiments, as shown in FIGS. 2 and 3, an implant 20 delivered by the system 10 can be a braid ball. The braid ball 20 can be formed from tubular braid stock including a resilient material, such as Nitinol, that defines an open volume (generally round, spherical, ovular, heart-shaped, etc.) in an uncompressed/unconstrained state. The size of the implant can be selected to fill an aneurysm 2, so the proximal end 53 of the device helps direct blood flow along the surface of the braid from which it is constructed to the branch vessels 8. A distal end 56 of the ball can be dome-shaped. The braid ball 20 can include a single layer or two layers 26, 28 (inner and outer layer, respectively) construction at least where impacted by flow at the neck 9 of the aneurysm 2. As shown, one or more turns of a coil (e.g., Pt wire) or a band (not shown) can provide a distal radiopaque feature to mark the location of the implant 20. Some exemplary implants that can be used in conjunction with the systems described herein are disclosed at U.S. Pub. No. 2013/0123830, published on May 16, 2013, the entirety of which is incorporated herein by reference.

According to some embodiments, the implant 20 can include a hub 50 at a proximal end 53 thereof. The hub 50 can be fixedly attached to the remainder of the implant 20. For example, the hub 50 can grasp braided filaments of the layers 26, 28 of the implant 20. The hub 50 can provide an aperture 54 for receiving engagement and release mechanisms of a delivery system.

According to some embodiments, the implant 20 can be set within an aneurysm sac 2 at a vascular bifurcation 4, formed by trunk vessel 6 and efferent vessels 8. The implant 20 can be delivered by access through the trunk vessel 6 (e.g., the basilar artery), preferably through a commercially available microcatheter with a delivery system as detailed below. To deliver the implant 20, the pusher sleeve 12 is positioned such that the implant 20 can be delivered at least partially into the aneurysm sac 2. After final positioning is achieved as shown in FIG. 3, engagement members are released from the implant 20 (e.g., from a hub 50 of the implant 20), as discussed further herein. Finally, the pusher sleeve 12 is withdrawn into the delivery catheter 48.

While the implant 20 can be a braid ball as illustrated herein, the implant 20 can have any other form or structure, according to various embodiments. For example, the implant 20 can be a vasoocclusive coil, a cylindrical, tube-like stent, or a filter. Other types of implants are generally known. The subject technology can be applied to any such implant for delivery and detachment thereof. For example, a given implant can include a hub 50 for engagement and release by a delivery system, as disclosed further herein.

Traditional electrolytic detachment members are generally a single wire with a constant diameter. These detach wires are generally as drawn and are very corrosion resistant due to the crystalline structure. Generally, when these detach wires are used they will leave behind small particulates and these particulates interfere with MRI imaging and also could lead to secondary stroke if particulates flow to distal vessels. Detachment time can be reduced by concentrating erosion to a limited area.

Figure 5:
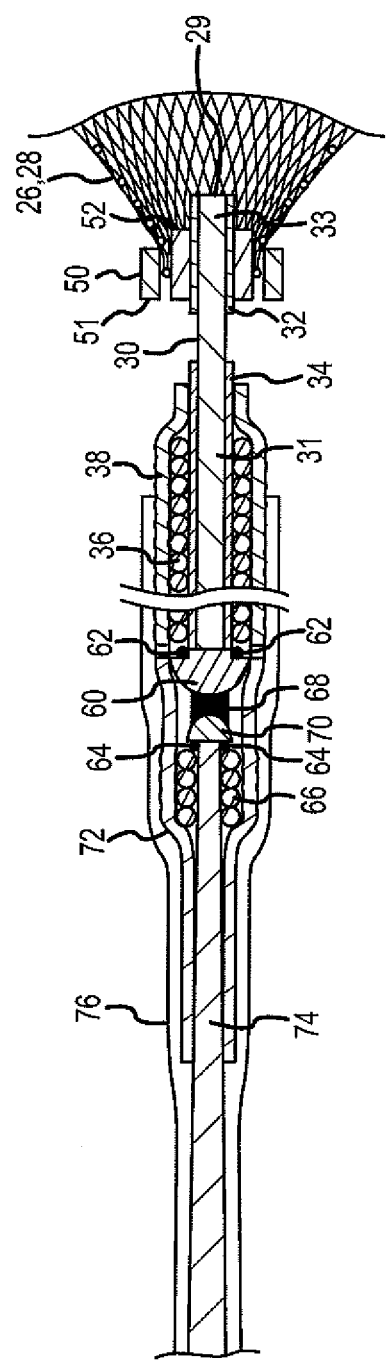
FIG. 5 shows a sectional view of a distal end of a delivery system, in accordance with one or more embodiments of the present disclosure.

According to some embodiments, as shown in FIGS. 4 and 5, a delivery system 10 includes an electrolytically corrodible core wire 29, having a proximal portion 31, a distal portion 33, and a detachment zone 30 is between the proximal portion 31 and the distal portion 33. At least a portion of the core wire 29, including the detachment zone 30, can be coated with a conductive material, such as carbon, gold, platinum, tantalum, combinations thereof, and the like. One or more metallic coatings can be applied using known plating techniques.

The core wire 29, including the detachment zone 30, can include one or more of the following materials: ceramic materials, plastics, base metals or alloys thereof, and preferably stainless steel. Some of the most suitable material combinations for forming the electrolytically corrodible points can include one or more of the following: stainless steels, preferably of the type AISI 301, 304, 316, or subgroups thereof; Ti or TiNi alloys; Co-based alloys; noble metals; or noble metal alloys, such as Pt, Pt metals, Pt alloys, Au alloys, or Sn alloys. Further, ceramic materials and plastics employed for forming the medical device can be electrically conductive.

According to some embodiments, portions of the core wire 29 can be coated with a nonconductive material. A proximal insulating layer 34 can be provided over at least a portion of an outer surface of the proximal portion 31 of the core wire 29. For example, the proximal insulating layer 34 can circumferentially surround an outer surface of the proximal portion 31. A distal insulating layer 32 can be provided over at least a portion of an outer surface of the distal portion 33 of the core wire 29. For example, the distal insulating layer 32 can circumferentially surround and contact an outer surface of the distal portion 33. The proximal and distal insulating layers 34, 32 can be of an electrically nonconductive or insulative polymer, such as polyimide, polypropylene, polyolefins, combinations thereof, and the like.

According to some embodiments, proximal and distal insulating layers 34, 32 leave exposed the detachment zone 30 of the core wire 29. When in contact with a body fluid, such as blood, the fluid serves as an electrolyte allowing current to be focused on the non-coated detachment zone 30. The proximal and distal insulating layers 34, 32 prevent exposure of the proximal portion 31 and distal portion 33 to the fluid. Accordingly, electrical energy conducted along the core wire 29 is concentrated at the detachment zone 30, thereby reducing the time required to erode away the detachment zone 30. The proximal and distal insulating layers 34, 32 can be over-molded, co-extruded, sprayed on, or dip-coated with respect to the core wire 29.

Laser ablation can be employed to selectively remove the coating to a controlled length minimizing the time required to erode through the component. Lengths as small as 0.0005" and as large as 0.1" or longer can be removed. According to some embodiments, lengths of detachment zone 30 can be greater than 0.005" and/or less than 0.010" to provide sufficient exposure to achieve detachment times of less than 30 seconds.

According to some embodiments, the distal insulating layer 32 is disposed radially between the distal portion 33 of the core wire 29 and the hub 50 of an implant 20. As shown in FIG. 5, an inner band 52 of the hub 50 circumferentially surrounds and contacts the distal insulating layer 32. An outer band 51 surrounds the inner band 52, such distal portions of the layers 26, 28 of the implant 20 are grasped between the inner and outer bands 52, 51 of the hub 50.

As shown in FIG. 5, the distal insulating layer 32 electrically isolates the implant 20 from an electrical charge conducted along a length of the core wire 29. A proximal end of the distal insulating layer 32 may be positioned proximal to the hub 50, and a distal end of the distal insulating layer 32 may be positioned distal to the hub 50. Likewise, a proximal end of the distal portion 33 may be positioned proximal to the hub 50, and a distal end of the distal portion 33 may be positioned distal to the hub 50, such that the distal portion 33 extends through and distally beyond a lumen formed by the hub 50. Alternatively, the proximal end of the distal insulating layer 32 may be coterminous with a proximal end of the hub 50, and/or a distal end of the distal insulating layer 32 may be coterminous with a distal end of the hub 50. Likewise, the proximal end of the distal portion 33 may be coterminous with a proximal end of the hub 50, and/or a distal end of the distal portion 33 may be coterminous with a distal end of the hub 50.

According to some embodiments, a distal marker coil 36 is wound helically about an outer surface of the proximal insulating layer 34. The distal marker coil 36 can be of a radiopaque material, such as platinum, gold, palladium, iridium, and alloys thereof. The distal marker coil 36 terminates at a proximal end thereof adjacent to a core wire end cap 60. The distal marker coil 36 can be between about 10 and about 40 mm in length, for example, about 30 mm. The distal marker coil 36 can be attached to the core wire end cap 60 by one or more welds 62. The core wire end cap 60 can be in physical contact and electrical conduction with the core wire 29.

An insulative layer 38 can be provided about an outer surface of the distal marker coil 36. For example, as shown in FIG. 5, the insulative layer 38 can extend over an entire length of the distal marker coil 36 and distally beyond the distal marker coil 36, such that every portion of the distal marker coil 36 is covered by the insulative layer 38. A distal end of the insulative layer 38 may contact and/or be adhered to the proximal insulating layer 34. The insulative layer 38 can be of an insulative biocompatible polymer material, such as polytetrafluoroethylene (PTFE). The insulative layer 38 may be shrink-wrapped over the corresponding portion of the delivery wire 10.

The distal marker coil 36 terminates at a proximal end thereof adjacent to a core wire end cap 60. The distal marker coil 36 can be attached to the core wire end cap 60 by one or more welds 62. The core wire end cap 60 can be attached to a pusher wire end cap 70, located at a distal end of a pusher wire 74.

According to some embodiments, a proximal marker coil 66 is wound helically about an outer surface of the pusher wire 74. The proximal marker coil 66 can be of a radiopaque material, such as platinum, gold, palladium, iridium, and alloys thereof. The proximal marker coil 66 terminates at a distal end thereof adjacent to the pusher wire end cap 70. The proximal marker coil 66 can be about 1 mm in length. The proximal marker coil 66 can be attached to the pusher wire end cap 70 by one or more welds 64. The pusher wire end cap 70 can be in physical contact and electrical conduction with the pusher wire 74. The pusher wire end cap 70 and the core wire end cap 60 can be connected by an interface 68 (e.g., a weld), configured to provide an electrically conductive connection between the pusher wire end cap 70 and the core wire end cap 60. Furthermore, an interface 68 can provide sufficient column strength to transfer an axial force applied to the pusher wire 74 to the proximal portion 31 of the core wire 29.

According to some embodiments, an insulative cover 72 can be provided about an outer surface of the proximal marker coil 66. For example, as shown in FIG. 5, the insulative cover 72 can extend over an entire length of the proximal marker coil 66 and proximally beyond the proximal marker coil 66, such that every portion of the proximal marker coil 66 is covered by the insulative cover 72. A distal end of the insulative cover 72 may contact and/or be adhered to the pusher wire 74. The insulative cover 72 can be of an insulative biocompatible polymer material, such as polytetrafluoroethylene (PTFE). The insulative cover 72 may be shrink-wrapped over the corresponding portion of the delivery wire 10. The insulative cover 72 can be adjacent to or integral with the insulative layer 38. A cover 76 may be provided over at least a portion of the delivery wire 10, including portions of the insulative layer 38 and the insulative cover 72.

Figure 6:
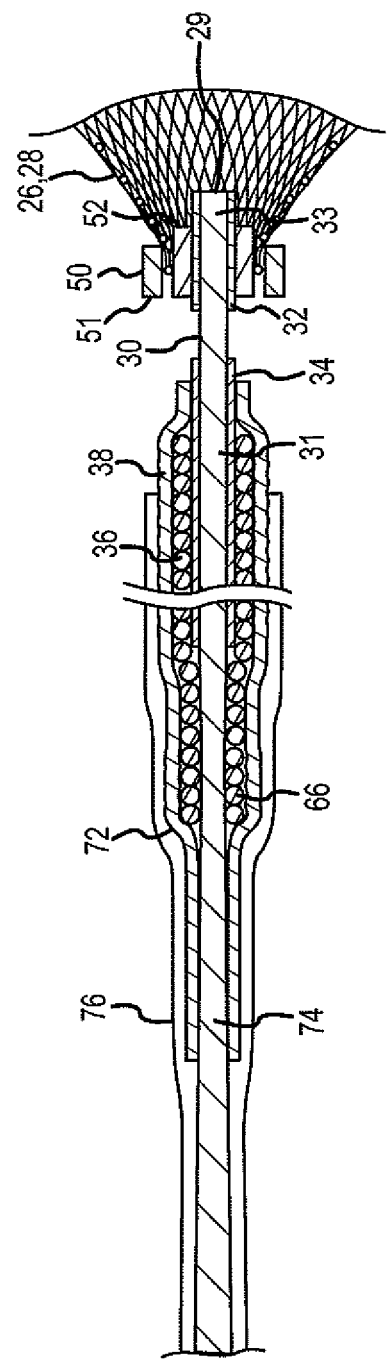
FIG. 6 shows a sectional view of a distal end of a delivery system, in accordance with one or more embodiments of the present disclosure.

According to some embodiments, as shown in FIG. 6, a pusher wire 74 can be integrally connected to the proximal portion 31 of the core wire 29. Accordingly, an electric charge applied to the pusher wire 74 can be conducted through the pusher wire 74, the proximal portion 31 of the core wire 29, and the detachment zone 30. Furthermore, an axial force applied to the pusher wire 74 can result in an axial movement of the core wire 29 and the implant 20.

According to some embodiments, as shown in FIG. 7, the core wire 29 can include an anchor end 27 at a terminal distal end of the core wire 29. The anchor end 27 can be located distal to the hub 50. For example, the anchor end 27 can be located within an interior portion of the implant 20. The anchor end 27 can have a maximum cross-sectional dimension that is greater than an inner cross-sectional dimension of the inner band 52. Accordingly, the core wire 29 is prevented from moving proximally entirely through the inner band 52. For example, an interface between the distal insulating layer 32 and the inner band 52 or an interface between the distal insulating layer 32 and the core wire 29 may allow a degree of movement of the core wire 29 relative to the inner band 52. To prevent the core wire 29 from being removed distally from within the inner band 52, the anchor end 27 can be of a size that cannot pass entirely proximally through the inner band 52.

According to some embodiments, a detachment zone 30 can be configured such that the corrodible portion thereof defines a unique structure configured to enhance electrolytic corrosion while preserving the structural characteristics thereof, A reduction in corrosion resistance will reduce a time required to deploy an intravascular and/or intrasaccular implant, thus reducing the overall procedure time. According to some embodiments, corrosion resistance of detachment zone 30 is decreased by exposure to laser or other energy, causing the detachment zone 30 to be structurally modified by heat. As a result, the detachment zone 30 will have a different microstructure than the material outside of the zone (e.g., the proximal portion 31 and/or the distal portion 33 of the core wire 29). The result will decrease the time to electrolytically plate off the material, resulting in faster detachment times.

The laser energy will create surface defects for a reduction in corrosion resistance. The laser energy will also alter the microstructure at a specific area, leading to a non-uniform corrosion rate. Accordingly, the preferred corrosion site can have a faster detach time.

According to some embodiments, the proximal portion 31 and/or the distal portion 33 have a microstructure with a crystallinity that is greater than a crystallinity of a microstructure of the detachment zone 30. According to some embodiments, the detachment zone 30 comprises a microstructure that is more amorphous than each of (i) a microstructure of the proximal portion 31 and (ii) a microstructure of the distal portion 33. According to some embodiments, a method of treating a delivery system includes providing an electrolytically corrodible core wire 29 comprising a proximal portion 31, a distal portion 33, and a detachment zone 30 between the proximal portion 31 and the distal portion 33. The detachment zone 30 is treated to produce a microstructure in the detachment zone 30 that is more amorphous than each of (i) a microstructure of the proximal portion 31 and (ii) a microstructure of the distal portion 33.

According to some embodiments, a detachment zone 30 can be configured such that the corrodible portion thereof defines a unique surface structure or texture configured to enhance electrolytic corrosion while preserving the structural characteristics thereof.

For example, the cross-sectional profile of the detachment zone can define at least one concavity, valley, recess, and/or indentation formed therein. In accordance with some embodiments, the cross-sectional profile of the detachment zone can define areas of positive curvature, such as one or more peaks, protrusions, and/or convexities, with areas of negative curvature, such as one or more valleys, recesses, concavities, and/or indentations. The one or more peaks, protrusions, and/or convexities and the one or more valleys, recesses, concavities, or indentations can be formed from surface structures such as grooves, channels, pits, threads, elongate troughs, circumferential or annular grooves, slots, apertures, coils, crimped ribbon, slotted ribbon, perforated ribbon, and/or other such structures that are precisely or randomly arranged. The shape of the cross-sectional profile of the connector body can be defined by one or more linear edges, parallel linear edges, intersecting linear edges, continuous curves, and/or combinations thereof.

By providing a surface structure or texture, some embodiments can thereby provide an increased surface area of the detachment zone in order to enhance the contact area of the component 206, reduce the overall volume of the detachment zone, and thereby improve the rate of corrosion. Further, various embodiments can be provided that are configured to provide excellent structural characteristics in order to ensure that the detachment zone is sufficiently robust and durable.

For example, in some embodiments, the component can have a component body comprising at least one structure, such as a trough, valley, recess, concavity, or indentation defining a recess surface area. In accordance with some embodiments, the component can be configured such that the valley, recess, concavity, or indentation can be used in the component without reducing structural characteristics of the component.

Further, the structure of the detachment zone can add recess surface area to the overall surface area of the detachment zone, thereby enhancing electrolytic corrosion of the detachment zone. Thus, the ratio of surface area to volume of the detachment zone can increase with an increase in overall surface area and a decrease in volume of the component. As discussed herein, the increase in the overall surface area of the detachment zone can be achieved by the incremental addition of surface area of the structure (e.g., the valley, recess, concavity, or indentation) versus the surface area of a surface without such a structure (e.g., a planar surface). The decrease in volume can be achieved by the addition of the void created by the valley, recess, concavity, or indentation.

Additionally, the detachment zone can be fabricated to provide features that will lead to an increased current density in one or more areas of the detachment zone. Such features can include, for example, ridges, edges, small radius corners, valleys, troughs, concavities, recesses, indentations, and/or other structures. In some embodiments, the presence of some of these structures on the detachment zone can reduce the local cross sectional area and/or otherwise contribute to the galvanic reaction. Features that increase current density can accelerate the galvanic reaction.

Additionally, according to some embodiments, the electrolytically corrodible detachment zone can be fabricated using a mechanical cold working operation. The cold working of the detachment zone can be performed through operations such as stamping, drawing, squeezing, bending, and/or other processes. The cold working of the detachment zone can enhance the galvanic reaction or corrosion. For example, as discussed herein, the detachment zone can comprise one or more structures or have a cross section that increases the surface area to volume ratio, which can enhance the galvanic reaction. Further, the process of cold working can alter the material properties of the detachment zone, which can improve the anodic quality or corrodibility of the detachment zone. Cold working can induce stresses in the material of the detachment zone, which can be released during the galvanic reaction, thus facilitating the galvanic reaction. Thus, fabrication of the detachment zone through a cold working operation can further enhance the galvanic reaction.

Furthermore, in accordance with some embodiments, the body of detachment zone can comprise a hollow portion that extends at least partially along the length of the body of detachment zone. The hollow portion can be formed as a discrete bubble or as an internal tubular vacuity extending within the body of detachment zone. In accordance with some embodiments, the tubular vacuity can extend longitudinally within the body of detachment zone. The hollow portion can define one or more sections that are exposed or open to an exterior of the connector body. Accordingly, in such embodiments, the rate of corrosion can be enhanced. Further, it is possible to thereby provide one or more areas where corrosion can be accelerated significantly as the corrosion process reaches the hollow portion(s) of the body of detachment zone. As such, one or more hollow portions can be present at one or more sections or points along the body of detachment zone.

Accordingly, in some embodiments, the presence of the surface structure(s) on the detachment zone can provide an increased ratio of surface area to volume, compared to a detachment zone that does not have such a structure. Thus, with a higher ratio of surface area to volume, the galvanic reaction can be faster, more predictable, and more effective for some embodiments.

Further, in some embodiments, the presence of a surface feature(s) on the detachment zone can provide increased current density at such feature(s), compared to a detachment zone that does not have such a feature(s). With a higher current density, the galvanic reaction can be faster, more predictable, and more effective for some embodiments.

Other features and discussion of electrolytically corrodible connections is provided in other applications of the present assignee, including the discussion and disclosure of U.S. Patent Application Publication No. 2012/0010648 and U.S. Pat. Nos. 7,323,000, and 8,048,104, the entirety of each of which is incorporated herein by reference.

Electrolytically non-corrodible sections of the delivery wire 44 can contain one or more of the following materials: noble metals or noble metal alloys, corrosion-resistant ceramic materials, corrosion-resistant plastics, and preferably platinum metal alloys.

The use of the above mentioned materials for the formation of electrolytically non-corrodible sections and of the electrolytically corrodible flanges ensures specific electrolytic corrosion of the flanges at the predetermined points.

In accordance with some embodiments, the electrolytically corrodible detachment zone can also be pre-corroded by etching or other methods. Thus, the structure(s) of a given cross-sectional profile can be modified to reduce the presence of corners, increase the recess depth, and/or otherwise enhance the corrosion rate. Further, various excellent structural designs can be provided to achieve desired corrosion performance through the teachings disclosed herein without pre-corrosion of the corrodible points.

Some embodiments can include a corrodible detachment zone that has a partial coating of a material to provide a greater or lesser electrochemical resistance. Thus, in embodiments that have one or more corrodible points, the electrochemical resistance of the points can be varied to achieve staged or preferential electrochemical resistance. Coatings of Zn, Sn, or alloys of such metals on fittings of stainless steel have been found to be particularly satisfactory. Further, some embodiments, the end of the delivery wire can be insulated, for example, by a material coating with reduced corrosion properties or a shrunk-on sleeve to improve its electrochemical resistance.

Embodiments disclosed herein can be used in veterinary or human medicine and more particularly, for the endovascular treatment of intracranial aneurysms and acquired or innate arteriovenous blood vessel deformities and/or fistulas and/or for the embolization of tumors by thrombozation.

The apparatus and methods discussed herein are not limited to the deployment and use of an occluding device within any particular vessels, but can include any number of different types of vessels. For example, in some aspects, vessels can include arteries or veins. In some aspects, the vessels can be suprathoracic vessels (e.g., vessels in the neck or above), intrathoracic vessels (e.g., vessels in the thorax), subthoracic vessels (e.g., vessels in the abdominal area or below), lateral thoracic vessels (e.g., vessels to the sides of the thorax such as vessels in the shoulder area and beyond), or other types of vessels and/or branches thereof.

In some aspects, the stent delivery systems disclosed herein can be deployed within superthoracic vessels. The suprathoracic vessels can comprise at least one of intracranial vessels, cerebral arteries, and/or any branches thereof. In some aspects, the stent delivery systems disclosed herein can be deployed within intrathoracic vessels. The intrathoracic vessels can comprise the aorta or branches thereof. In some aspects, the stent delivery systems disclosed herein can be deployed within subthoracic vessels. In some aspects, the stent delivery systems disclosed herein can be deployed within lateral thoracic vessels.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A delivery system, comprising:
   an electrolytically corrodible core wire comprising a proximal portion, a distal portion, and a detachment zone between the proximal portion and the distal portion;
   a proximal insulating layer annularly contacting the proximal portion;
   a coil helically winding about and contacting at least a portion of the proximal insulating layer;
   a tube annularly contacting at least a portion of the helical coil;
   a distal insulating layer annularly contacting the distal portion; and
   a hub of an implant annularly contacting at least a portion of the distal insulating layer,
   wherein the proximal portion and the distal portion each have a microstructure with a crystallinity that is greater than a crystallinity of a microstructure of the detachment zone.

2. The delivery system of claim 1, wherein the detachment zone has an axial length that is less than 0.010 inches.

3. The delivery system of claim 1, wherein the detachment zone has an axial length greater than or equal to 0.005 inches and less than 0.010 inches.

4. The delivery system of claim 1, wherein the core wire comprises an anchor end that is distal to a distalmost end of the hub, the anchor end having a maximum cross-sectional dimension that is greater than an inner cross-sectional dimension of a lumen of the hub.

5. The delivery system of claim 1, wherein the detachment zone is axially between the proximal portion and the distal portion.

6. A delivery system, comprising:
   an electrolytically corrodible core wire comprising a proximal portion, a distal portion, and a detachment zone between the proximal portion and the distal portion:
   a proximal insulating layer annularly contacting the proximal portion;
   a coil helically winding about and contacting at least a portion of the proximal insulating layer;
   a tube annularly contacting at least a portion of the helical coil;
   a distal insulating layer annularly contacting the distal portion; and
   a hub of an implant annularly contacting at least a portion of the distal insulating layer,
   wherein the detachment zone comprises a microstructure that is more amorphous than each of (i) a microstructure of the proximal portion and (ii) a microstructure of the distal portion.

7. A delivery system, comprising:
   an electrolytically corrodible core wire comprising a proximal portion, a distal portion, and a detachment zone between the proximal portion and the distal portion;
   a proximal insulating layer annularly contacting a proximal portion; and
   a distal insulating layer annularly contacting a distal portion;
   wherein a distal end of the proximal insulating layer and a proximal end of the distal insulating layer are axially spaced apart to expose the detachment zone;
   wherein the detachment zone comprises a microstructure that is more amorphous than each of (i) a microstructure of the proximal portion and (ii) a microstructure of the distal portion.

8. The delivery system of claim 7, wherein the proximal portion, the detachment zone, and the distal portion are of a conductive material.

9. The delivery system of claim 7, wherein the detachment zone is axially between the proximal portion and the distal portion.

10. The delivery system of claim 7, wherein the proximal portion and the distal portion each have a microstructure with a crystallinity that is greater than a crystallinity of a microstructure of the detachment zone.

11. The delivery system of claim 7, further comprising:
    a coil helically winding about and contacting at least a portion of the proximal insulating layer; and
    a tube annularly contacting at least a portion of the helical coil.

12. The delivery system of claim 7, further comprising a hub of an implant annularly contacting at least a portion of the distal insulating layer.

13. The delivery system of claim 12, wherein the core wire comprises an anchor end that is distal to a distalmost end of the hub, the anchor end having a maximum cross-sectional dimension that is greater than an inner cross-sectional dimension of a lumen of the hub.

14. The delivery system of claim 7, wherein the detachment zone has an axial length that is less than 0.010 inches.

15. The delivery system of claim 7, wherein the detachment zone has an axial length greater than or equal to 0.005 inches and less than 0.010 inches.

* * * * *